(12) United States Patent
Schneider

(10) Patent No.: US 10,912,529 B2
(45) Date of Patent: Feb. 9, 2021

(54) DETERMINING A REMAINING TIME DURING MEDICAL IMAGING

(71) Applicant: Rainer Schneider, Erlangen (DE)

(72) Inventor: Rainer Schneider, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 258 days.

(21) Appl. No.: 15/650,346

(22) Filed: Jul. 14, 2017

(65) Prior Publication Data

US 2018/0014803 A1    Jan. 18, 2018

(30) Foreign Application Priority Data

Jul. 14, 2016 (DE) .................. 10 2016 212 877

(51) Int. Cl.
*A61B 6/00* (2006.01)
*G16H 20/40* (2018.01)
*G01R 33/28* (2006.01)
*G16H 40/63* (2018.01)
*A61B 5/055* (2006.01)
*A61B 6/03* (2006.01)
*G06F 3/0484* (2013.01)

(52) U.S. Cl.
CPC .............. *A61B 6/465* (2013.01); *A61B 5/055* (2013.01); *G01R 33/288* (2013.01); *G16H 20/40* (2018.01); *G16H 40/63* (2018.01); *A61B 6/032* (2013.01); *A61B 6/037* (2013.01); *G06F 3/0484* (2013.01)

(58) Field of Classification Search
CPC ......... A61B 6/465; A61B 5/055; A61B 6/032; A61B 6/037; G16H 20/40; G16H 40/63; G01R 33/288; G06F 3/0484
See application file for complete search history.

(56) References Cited

U.S. PATENT DOCUMENTS

| 5,861,865 A * | 1/1999 | Anand ................... A61B 5/055 174/350 |
| 2002/0114423 A1* | 8/2002 | Grass ....................... A61B 6/12 378/4 |
| 2008/0317205 A1* | 12/2008 | Inuga ................... A61B 6/4441 378/97 |
| 2009/0154647 A1* | 6/2009 | Matsuzawa ............ A61B 6/032 378/98 |
| 2015/0078528 A1 | 3/2015 | Okada |
| 2016/0187436 A1* | 6/2016 | Piron ................. G01R 33/3858 600/411 |

(Continued)

OTHER PUBLICATIONS

German Office Action for German Application No. 102016212877.9 dated Mar. 10, 2017, with English Translation.

(Continued)

*Primary Examiner* — Christine S. Kim
(74) *Attorney, Agent, or Firm* — Lempia Summerfield Katz LLC

(57) ABSTRACT

A method for determining a current remaining time during a measurement for the purpose of medical imaging, an evaluation unit, a medical imaging device, and a computer program product are provided. The method provides for a permitted operating range and an item of extrapolation information regarding the critical event to be provided. The current remaining time is determined by an evaluation unit based on the permitted operating range and the item of extrapolation information.

14 Claims, 3 Drawing Sheets

(56) References Cited

U.S. PATENT DOCUMENTS

2017/0156689 A1* 6/2017 Shinotsuka ............ A61B 6/461

OTHER PUBLICATIONS

Vinding, Mads S., et al. "Local SAR, global SAR, and power-constrained large-flip-angle pulses with optimal control and virtual observation points." Magnetic resonance in medicine 77.1 (2017): 374-384.

* cited by examiner

DETERMINING A REMAINING TIME DURING MEDICAL IMAGING

This application claims the benefit of DE 10 2016 212 877.9, filed on Jul. 14, 2016, which is hereby incorporated by reference in its entirety.

BACKGROUND

The present embodiments relate to determining a current remaining time during a measurement for the purpose of medical imaging.

By using medical imaging, and, for example, by using magnetic resonance tomography (MRT) and/or computed tomography (CT) and/or X-ray photographs, the interior of a body of a patient may be mapped. To do this, in the case of magnetic resonance tomography, for example, rapidly switched gradient pulses are superimposed on a static basic magnetic field during a magnetic resonance measurement with a magnetic resonance device. The gradient pulses may give rise to undesirable peripheral nerve stimulation (PNS) in the body of the patient.

High-frequency excitation pulses (HF pulses) are beamed into the object under examination in order to trigger magnetic resonance signals. The energy of the HF pulses absorbed per unit of time and per kilogram of body weight in the course of this is usually referred to as the specific absorption rate (SAR). The absorption of the HF energy may result in a heating of the bodily tissue so that burns may occur in the case of inadmissibly high local concentration of the HF energy. In the case of uniform distribution of the HF energy over the whole body, the load on the thermoregulation or cardiac circulatory system of the patient, respectively, is definitive.

The energy absorption and/or the peripheral nerve stimulation are therefore potential critical events during a magnetic resonance examination that may be described by suitable parameters such as the SAR, for example. To prevent an endangerment of the patient, conventional magnetic resonance devices may have ways to bring about an immediate termination of the magnetic resonance measurement as soon as a parameter lies outside a permitted operating range.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method that enables an improved monitoring of at least one critical event during a measurement (e.g., of an interventional nature) for the purpose of medical imaging is provided.

In one embodiment, a method includes providing a permitted operating range and an item of extrapolation information regarding at least one critical event, based on which a current remaining time is determined by an evaluation unit. The method may be employed during a measurement for the purpose of medical imaging (e.g., a magnetic resonance measurement) in order to monitor the at least one critical event and/or in order to determine the current remaining time during an interventional procedure guided by MR for example.

Measurement for the purpose of medical imaging may include a capturing of measurement data (e.g., magnetic resonance data) based on which depictions of an object under examination may be generated.

The method may be employed for different imaging modalities, such as in the case of a magnetic resonance measurement and/or a computer tomography measurement and/or an X-ray measurement and/or a mammography measurement and/or a positron emission tomography measurement and/or a single photon emission computer tomography measurement and/or a scintigraphy measurement and/or a sonography measurement and/or a thermography measurement and/or an electrical impedance tomography measurement, for example.

The method of carrying out a magnetic resonance measurement may be defined by using a pulse sequence (e.g., a time-based sequence of HF pulses and gradient pulses for exciting an image volume to be measured) for signal generation, and local coding. Depending on the pulse sequence, different contrasts such as T1, T2 or susceptibility weighting may be set, for example. Additionally, field of view (FoV), resolution, and layer thickness may be set among other aspects.

The at least one critical event may include an energy absorption (e.g., a heating of at least one part of a patient's body caused as a result) and/or a peripheral nerve stimulation (PNS) in a patient's body, for example. The energy absorption may occur, for example, due to a nuclear spin resonance in the case of a magnetic resonance measurement and/or a radiation absorption in the case of an X-ray measurement. The at least one critical event may be described with the aid of at least one parameter. For example, an energy absorption may be described with the SAR and/or a radiation dose as a parameter.

The permitted operating range may be described by at least one limit value for the at least one parameter of the at least one critical event, for example, by a maximum specific absorption rate and/or a maximum gradient change rate. The magnetic resonance device may operate in the permitted operating range as long as the at least one limit value is satisfied. The permitted operating range is advantageously realized such that no endangerment arises for the patient during the measurement for the purpose of medical imaging (e.g., a magnetic resonance measurement) by the operation of the medical imaging device (e.g., a magnetic resonance device) within the permitted operating range. The permitted operating range may be stored in a database that is saved on a hard disk and/or in a network, for example and may be transferred from there to the evaluation unit.

The extrapolation information may be suitable for making an estimation about the remaining time. The extrapolation information may include information that refers to earlier and/or instantaneous parameters (e.g., measured values) of the critical event.

The earlier parameters are primarily understood to be parameters that relate to time points lying in the past at the time point when the extrapolation information is provided. The instantaneous parameters are primarily understood to be parameters that relate essentially to the time point when the extrapolation information is provided.

Thus for example, conclusions about the further progression of the critical event may be drawn from earlier and/or instantaneous parameters of the critical event on the assumption that the critical event will also continue to develop in that way.

For example, the parameters are captured with the aid of a measurement and stored. In this regard, a parameter may be an instantaneous parameter at the time point of capture.

Over time, therefore, access may be had to a large number of parameters that are past (e.g., earlier) at that time.

The extrapolation information may include information that refers to earlier and/or instantaneous and/or future boundary conditions (e.g., sequence information) of the critical event. For example, all measurement parameters of the measurement for the purpose of medical imaging (e.g., the magnetic resonance measurement) that exert an influence on the critical event may be seen as boundary conditions in this regard.

The earlier boundary conditions are primarily understood to be boundary conditions that relate to time points and/or have an effect at time points lying in the past at the time point when the extrapolation information is provided. The instantaneous boundary conditions are may be boundary conditions that relate essentially to the time point when the extrapolation information is provided and/or have an effect at that time point. The future boundary conditions may be boundary conditions that relate to time points and/or have an effect at time points lying in the future at the time point when the extrapolation information is provided.

Thus, for example, even better conclusions about the further progression of the critical event may be drawn from earlier and/or instantaneous parameters of the critical event while taking account of the earlier and/or instantaneous and/or future boundary conditions of the critical event. Thus, for example, evolving boundary conditions may also be taken into account in the determination of the current remaining time.

The extrapolation information may be stored in a database that is saved on a hard disk and/or in a network, for example, and may be transferred from the database to the evaluation unit.

The evaluation unit may include an arithmetic-logic unit (e.g., with one or a plurality of processors, and/or a memory unit such as one or a plurality of storage media).

A remaining time may be an as yet unexpired time. The current remaining time may be a time duration that specifies how long the measurement for the purpose of medical imaging (e.g., the magnetic resonance measurement) may be continued as a minimum without departing from the permitted operating range (e.g., without changing a pulse sequence prevailing at that instant).

The determination of the current remaining time may be carried out multiple times (e.g., continuously and/or regularly). The current remaining time may be updated constantly (e.g., at least once per minute, at least 10 times per minute, or at least 100 times per minute).

The current remaining time may be displayed, for example, to an operator and/or a physician to enable an effective monitoring of the at least one critical event during the measurement for the purpose of medical imaging (e.g., a magnetic resonance measurement). The display may be effected by using a display unit, such as a screen, for example. Where appropriate, the operator and/or a physician may intervene in a timely manner in the measurement event, for example, to prevent an injury to the patient.

An embodiment of the method provides for a minimum remaining time to be provided that is compared with the current remaining time. An output signal is output as a function of an outcome of this comparison of the current remaining time with the minimum remaining time.

The minimum remaining time may be provided with the aid of an input unit, such as a keyboard and/or a computer mouse, for example. The minimum remaining time may be provided, for example, by a physician prior to starting the measurement for the purpose of medical imaging (e.g., a magnetic resonance measurement). The minimum remaining time may be chosen such that the operator and/or the physician has enough time to influence the measurement for the purpose of medical imaging in such a manner (e.g., to terminate the measurement for the purpose of medical imaging) that the patient suffers no harm.

For example, the output signal may have an acoustically perceptible signal (e.g., a beep). Accordingly, the output unit may include a loudspeaker, for example. For example, the output signal may be correlated with the current remaining time such that a volume and/or a pitch and/or a repetition rate of the output signal are dependent on the current remaining time.

The output signal may also have a visually perceptible signal (e.g., a bar). Accordingly, the output unit may include a display, for example. For example, the output signal may be correlated with the current remaining time such that a size and/or a color and/or a repetition rate of the output signal are dependent on the current remaining time.

The output of the output signal as a function of the outcome of the comparison of the current remaining time with the minimum remaining time may include, for example, an output signal only being output if the current remaining time is less than the minimum remaining time. The, for example, perceptible output of the output signal is therefore not absolutely necessary for every comparison outcome. For example, if the outcome of the comparison is that the current remaining time is less than the minimum remaining time, a warning signal may be output as an output signal. If the current remaining time is more than the minimum remaining time, an output of an output signal may be omitted. An output signal (e.g., one that is perceptible to the operator and/or the physician) may thus not be output in every eventuality but instead only in the case of certain outcomes of the comparison.

Based on the comparison of the current remaining time with the minimum remaining time by the evaluation unit, the at least one critical event may be effectively monitored during the measurement for the purpose of medical imaging (e.g., a magnetic resonance measurement).

An embodiment of the method provides for a position of an interventional instrument to be displayed during the measurement for the purpose of medical imaging (e.g., a magnetic resonance measurement). An interventional procedure may be carried out during the measurement for the purpose of medical imaging. In the case of an interventional procedure, for example, a therapeutic procedure (e.g., in the vascular and/or biliary system and/or in parenchymatous organs of a patient) is performed under image control.

As a result of the imaging, the interventional procedure may be guided. For example, a position of an interventional instrument such as, for example, a catheter, a balloon, a radio frequency probe, a needle, a biopsy instrument, etc. in the body of the patient may be displayed, for example, to a physician so that the interventional instrument may be directed in the body of the patient.

The minimum remaining time may be chosen such that the minimum remaining time is sufficient to safely interrupt and/or break off the interventional procedure in an emergency (e.g., by safely removing the interventional instrument from the body of the patient and/or safely evacuating the patient). For example, the patient may be transitioned in to a safe condition in this time in which further imaging is no longer necessary and/or may be temporarily halted.

In the case of interventional procedures, a current identification of the current remaining time may be advantageous since the measurement for the purpose of medical imaging (e.g., a magnetic resonance measurement) is frequently interrupted and driven by circumstances. In contrast to any conventional a-priori appraisals prior to starting the measurement for the purpose of medical imaging, unforeseeable circumstances during an interventional procedure may also be taken into account during the monitoring of the at least one critical event.

For the purpose of determining the current remaining time, an appraisal of the critical event (e.g., a progression of the critical event) may be generated based on the extrapolation information.

The extrapolation information may include at least one value determined by measurement (e.g., an online SAR value). The at least one value determined by measurement may be a parameter of the critical event. For example, the at least one value determined by measurement may be a measured value itself and/or a value derived from the measured value.

The online SAR value may be an instantaneous SAR value describing the SAR at the time point when the SAR is determined. The determination of an online SAR value may include a capturing of a power radiated by the magnetic resonance device and a reflected power, for example, with the online SAR value generally being the difference between the radiated and the reflected power. Suitable sensors for capturing the radiated and the reflected power are known from the state of the art.

The current remaining time may be determined by an extrapolation from earlier and/or instantaneous online SAR values. It is assumed in this regard, for example, that the development of the earlier and/or instantaneous online SAR values is constant.

A further embodiment provides for the extrapolation information to include an item of sequence information. The at least one item of sequence information may be an earlier and/or instantaneous and/or future boundary condition of the critical event. So the estimation of the current remaining time may include an extrapolation (e.g., time-based) of the sequence information. The estimation may be achieved by a preview of the coming (e.g., all of the coming) pulse sequence. The current remaining time may therefore be identified particularly precisely.

The sequence information may include at least one measurement parameter of the pulse sequence that is used during the measurement for the purpose of medical imaging (e.g., a magnetic resonance measurement such as a repetition time (TR), an echo time (TE), a repetition time (TR), and/or a flip angle). A pulse sequence may be a time-based sequence of HF pulses and gradient pulses for exciting the image volume to be measured, for signal generation, and local coding. The sequence information may be stored (e.g., in the form of a sequence protocol) in a database that is saved on a hard disk and/or in a network, for example, and may be transferred from the database to the evaluation unit.

The at least one value determined by measurement and the sequence information are combined. Thus, an estimation of the coming SAR values may be performed based on earlier and/or instantaneous online SAR values, for example. The estimation is adapted based on the sequence information. For example, if it is evident from the sequence information that another protocol should be used in the further progression that, for example, provides for a higher SAR load then the current remaining time may be correspondingly reduced.

For example, a dependency between the sequence information and the critical event may be calibrated with the aid of the at least one value determined by measurement. The accuracy of the current remaining time may therefore be increased. For example, if a specific online SAR value is determined for a specific partial sequence of the pulse sequence, then that specific partial sequence may be calibrated to that specific online SAR value. In the eventuality that the specific partial sequence occurs further and/or again in the further progression of the magnetic resonance measurement, then that specific online SAR value may thus be used as the basis for the determination of the current remaining time.

For example, at the start of measurement for the purpose of medical imaging (e.g., a magnetic resonance measurement), at which time point earlier parameters (e.g., online SAR values) are not yet available, the current remaining time may be estimated based on the sequence information that advantageously describes the impending sequence progression.

The determination of the current remaining time may include an averaging (e.g., of the extrapolation information). For example, earlier parameters such as, for example, the online SAR values may be averaged. The value resulting from this averaging may be used as the basis for the extrapolation of the future SAR values. An averaging makes it possible to increase the accuracy and/or robustness of the extrapolation.

In one embodiment, different SAR estimations generated based on the sequence information, for example, by previewing the coming pulse sequence may be averaged.

An embodiment provides for the determination of a current remaining time to include a worst-case view. A worst-case view may provide for the smaller remaining time to be chosen as the current remaining time in the case of a determination of a remaining time according to different methods (e.g., by an estimation based on the sequence information and an estimation based on the online SAR values). A particularly safe current remaining time may therefore be determined.

The estimation may be carried out at least partly prior to starting the measurement for the purpose of medical imaging (e.g., a magnetic resonance measurement). The computing capacity of the evaluation unit may therefore be fully utilized in a particularly effective manner since possible computing steps no longer have to be carried out online during the magnetic resonance measurement.

As already described, an embodiment of the method provides for a warning message to be output as an output signal in the case of the current remaining time being less than the minimum remaining time. As a result, it is possible to respond to the situation as quickly as possible.

A further embodiment of the method provides for a pulse sequence (e.g., at least one measurement parameter of the pulse sequence) to be changed depending on the outcome of the comparison of the current remaining time with the minimum remaining time (e.g., in the case of the current remaining time being less than the minimum remaining time). Advantageously, changing the pulse sequence makes it possible for the critical event to be favorably influenced to increase the current remaining duration.

Changing the pulse sequence may include changing at least one measurement parameter of the pulse sequence such as, for example, a repetition time (TR), and/or a flip angle, and/or a transmit voltage, and/or a transmit mode in the case of parallel transmission. Adapting these measurement parameters makes it possible, for example, for the SAR to be reduced.

Repetition time (TR) may be the time between two excitation pulses. The flip angle may identify the deflection of the magnetization from the longitudinal direction after the end of an HF pulse. Using the transmit voltage, the electromagnetic energy emitted by transmit antennas may be influenced. If a large number of transmit channels are employed, then the transmit mode may be adapted in the case of parallel transmission (pTx) in order, for example, to reduce the SAR. A possible method for optimizing pTx transmit operation is described in Vinding, M. S. et al., Local SAR, Global SAR, and Power☐Constrained Large☐Flip☐Angle Pulses with Optimal Control and Virtual Observation Points, *Magnetic resonance in medicine*, 2015.

A further variant of the method provides for at least one changed measurement parameter to be restored in the case of the current remaining time being less than a minimum remaining time extended by a safety margin.

The safety margin may be provided to the evaluation unit, for example, in the same way as the minimum remaining time.

An evaluation unit that is realized to carry out a method for determining a current remaining time during a measurement for the purpose of medical imaging (e.g., to determine a current remaining time based on a permitted operating range and an item of sequence information) is provided. Additionally, a medical imaging device with an evaluation unit of such a type is provided. For example, the medical imaging device may include a magnetic resonance device and/or a computer tomography device and/or an X-ray device and/or a mammography device and/or a positron emission tomography device and/or a single photon emission computer tomography device and/or a scintigraphy device and/or a sonography device and/or a thermography device and/or an electrical impedance tomography device.

The advantages of the evaluation unit and the magnetic resonance device essentially correspond to the advantages of the method for determining a current remaining time during a measurement for the purpose of medical imaging that are set forth in detail above and below. Features, advantages, or alternative embodiments referred to in this regard may likewise be transposed to the other subject matters and vice versa.

In other words, the subject-matter may also be developed with the features that are described in connection with a method for determining a current remaining time during a measurement for the purpose of medical imaging. In this regard, the corresponding functional features of the method are realized by corresponding subject-matter modules (e.g., by hardware modules).

Additionally, a computer program product that includes a program and may be loaded directly into a memory of a programmable arithmetic-logic unit of the evaluation unit, and has a program (e.g., libraries and help functions; instructions) to carry out a method for determining a current remaining time during a measurement for the purpose of medical imaging whenever the computer program product is executed in the arithmetic-logic unit of the evaluation unit is provided. In this regard, the computer program product may include a piece of software with a source code that still has to be compiled and bound or just has to be interpreted, or a piece of executable software code that still just requires loading into the evaluation unit for the purpose of being executed. The computer program product makes it possible for the method to be carried out rapidly, in an identically repeatable manner, and robustly. The computer program product is configured such that the computer program product may carry out the method steps by using the evaluation unit. In this regard, the evaluation unit in each case has the prerequisites such as, for example, a corresponding working memory, a corresponding graphics card, or a corresponding logic unit so that the respective method acts may be carried out efficiently. For example, the computer program product is stored on a computer-readable medium (e.g., a non-transitory computer-readable storage medium) or stored on a network or server.

Control information of the computer program product may be stored on an electronically readable data carrier. The control information on the electronically readable data carrier may be configured such that the electronically readable data carrier carries out a method for determining a current remaining time during a measurement for the purpose of medical imaging. Examples of electronically readable data carriers are a DVD, a magnetic tape, or a USB stick, on which electronically readable control information (e.g., software) is stored. When this control information is read from the data carrier and stored in an evaluation unit, all of the embodiments of the previously described methods may be implemented. Thus, one or more of the present embodiments may also start from the computer-readable medium and/or the electronically readable data carrier.

BRIEF DESCRIPTION OF THE DRAWINGS

Parts corresponding to each other are assigned the same reference symbols in all figures.

DETAILED DESCRIPTION

Figure 1:
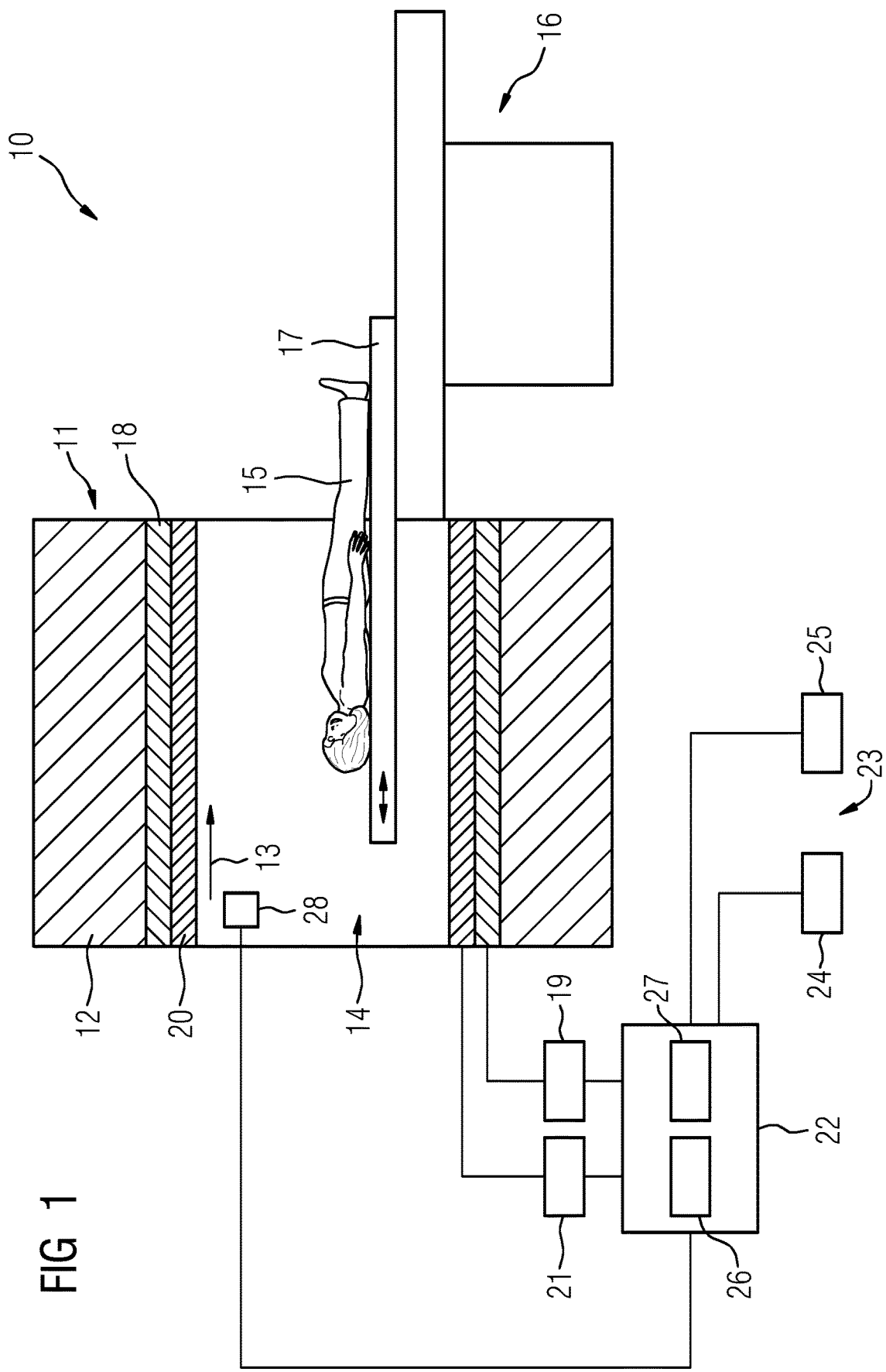
FIG. 1 shows a magnetic resonance device as an exemplary medical imaging device in a schematic representation.

FIG. 1 shows a schematic representation of a magnetic resonance device 10 by way of example for a medical imaging device. In place of the magnetic resonance device, however, other modalities may also be employed such as, for example, a computer tomography device, an X-ray device, a mammography device, a positron emission tomography device, a single photon emission computer tomography device, a scintigraphy device, a sonography device, a thermography device, an electrical impedance tomography device, or any combination thereof.

The magnetic resonance device 10 includes a magnet unit 11 having a main magnet 12 for a generation of a main magnetic field 13 that is strong and, for example, constant over time. Additionally, the magnetic resonance device 10 includes a patient recording zone 14 for a recording of a patient 15. In the present exemplary embodiment, the patient recording zone 14 is realized in a cylindrical manner and is surrounded in a peripheral direction by the magnet unit 11 in a cylindrical manner. In principle, however, a realization of the patient recording zone 14 that diverges may be provided. The patient 15 may be slid into the patient recording zone 14 by using a patient support device 16 of the magnetic resonance device 10. In this regard, the patient support device 16 has a patient table 17 configured so as to be capable of moving inside the patient recording zone 14.

The magnet unit 11 has a gradient coil unit 18 for a generation of magnetic field gradients that are used for local coding during an imaging process. The gradient coil unit 18 is controlled by using a gradient control unit 19 of the magnetic resonance device 10. The magnet unit 11 also includes a high-frequency antenna unit 20 that is realized in the present exemplary embodiment as a body coil permanently integrated into the magnetic resonance device 10. The high-frequency antenna unit 20 is configured for an excitation of atomic nuclei. This excitation is instigated in the main magnetic field 13 generated by the main magnet 12. The high-frequency antenna unit 20 is controlled by a high-frequency antenna control unit 21 of the magnetic resonance device 10 and beams high-frequency magnetic resonance sequences into an examination space that is essentially formed of a patient recording zone 14 of the magnetic resonance device 10. The high-frequency antenna unit 20 is also realized for receiving magnetic resonance signals.

The magnetic resonance device 10 has a system control unit 22 for controlling the main magnet 12, the gradient control unit 19, and for controlling the high-frequency antenna control unit 21. The system control unit 22 controls the magnetic resonance device 10 centrally (e.g., as in the implementation of a predetermined imaging gradient echo sequence). The system control unit 22 also includes a reconstruction unit, not represented in detail, for a reconstruction of medical image data captured during the magnetic resonance examination. The magnetic resonance device 10 also includes a user interface 23 that is connected to the system control unit 22. Control information such as, for example, imaging parameters and also reconstructed magnetic resonance images may be displayed on a display unit 24 (e.g., on at least one monitor) of the user interface 23 for a medical operator. The user interface 23 also has an input unit 25 by which information and/or parameters may be input by the medical operator during a measuring event.

The system control unit 22 includes an evaluation unit 27 for determining a current remaining time and a database 27 in which information about a permitted operating range of the magnetic resonance device 10 is stored and may be transmitted from the database 27 to the evaluation unit 26. The evaluation unit 27 may include a programmable arithmetic-logic unit (e.g., with one or a plurality of processors, and/or a memory unit; with one or a plurality of storage media that are not represented in detail). A program may be loaded into the memory of the programmable arithmetic-logic unit with a program to carry out one of the methods represented here whenever the program is executed in the arithmetic-logic unit.

The magnetic resonance device further includes a sensor unit 28 to determine at least one value by measurement that may be suitable for characterizing a critical event during a magnetic resonance measurement such as, for example, an energy absorption and/or a peripheral nerve stimulation of the patient 15. This at least one value may be transmitted to the evaluation unit 27 as extrapolation information.

For example, the sensor unit 28 may include at least one sensor that detects the power and/or energy emitted by the high-frequency antenna unit 20, and at least one further sensor that detects power and/or energy reflected from same. The power and/or energy absorbed by the body 15 (e.g., an online SAR value) may then be identified from the difference between these quantities. The sensor unit 28 may therefore function as a SAR sensor as well as in other ways.

Figure 2:
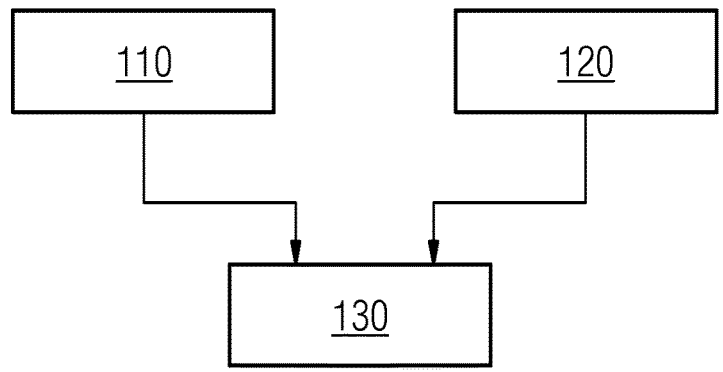
FIG. 2 shows a block representation of one embodiment of a method in a first variant.
Figure 3:
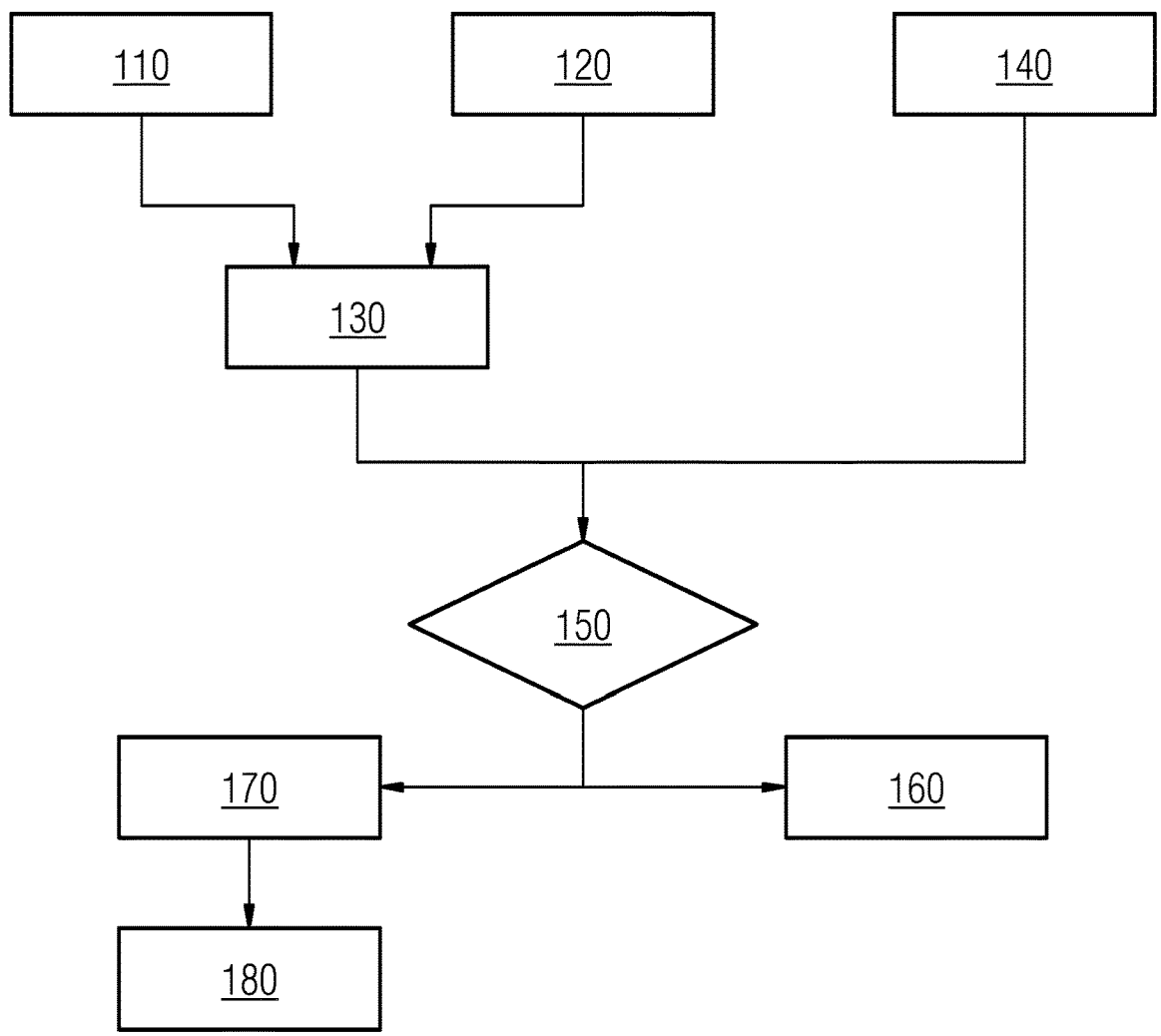
FIG. 3 shows a block representation of one embodiment of a method in an expanded variant.
Figure 4:
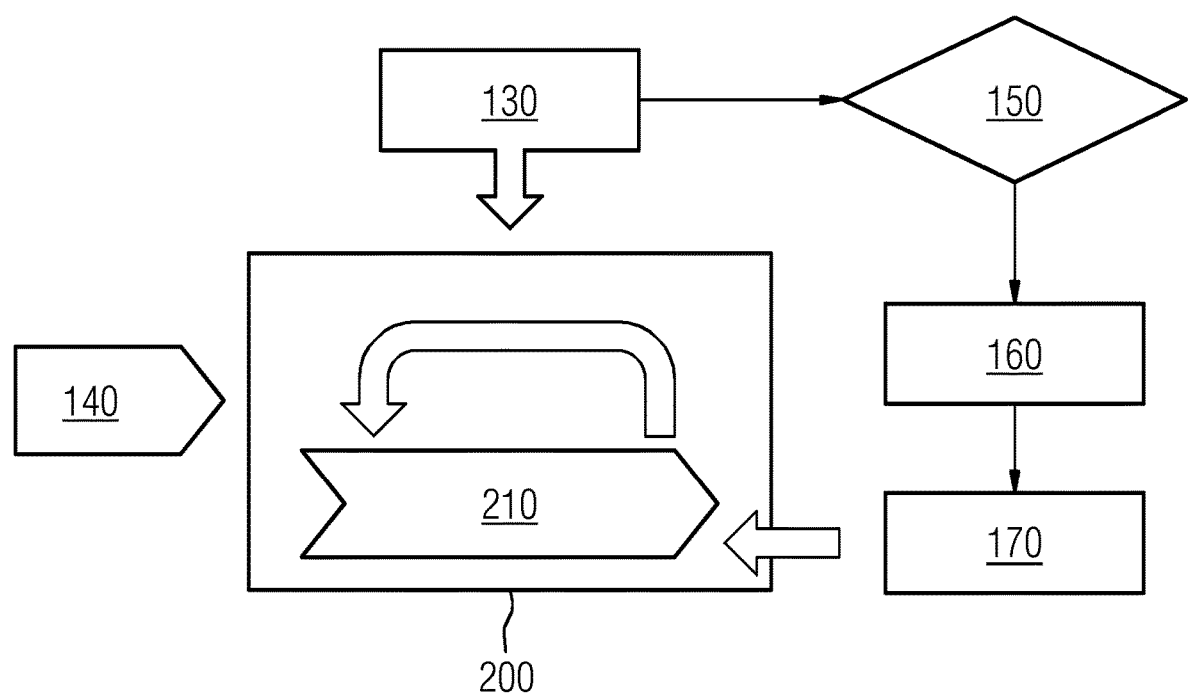
FIG. 4 shows a block representation of one embodiment of a method in a further variant.

FIGS. 2 to 4 show, by way of example, one embodiment of a method for determining a current remaining time during a measurement for the purpose of medical imaging. This exemplary embodiment refers to a magnetic resonance measurement as a measurement for the purpose of medical imaging, but the method may also be employed in the context of other measurement methods (e.g., a computer tomography measurement and/or an X-ray measurement and/or a mammography measurement and/or a positron emission tomography measurement and/or a single photon emission computer tomography measurement and/or a scintigraphy measurement and/or a sonography measurement and/or a thermography measurement and/or an electrical impedance tomography measurement).

In act 110, a permitted operating range is provided to the evaluation unit. The permitted operating range may include one or a plurality of limit values for the operation of the magnetic resonance device 10 (e.g., of the high-frequency antenna unit 20 and/or of the gradient coil unit 18).

In act 120, an item of extrapolation information is provided to the evaluation unit. The extrapolation information may include, for example, at least value determined by measurement based on the sensor unit 28 and/or an item of sequence information. An item of sequence information primarily includes parameter values of the MR sequence already implemented and/or waiting to be implemented. Estimations about an anticipated SAR load on the patient 15 may be derived from the same, for example.

In act 130, a current remaining time is determined based on the permitted operating range and the extrapolation information by the evaluation unit. In this regard, the current remaining time may be a time duration for the length of which a continuous imaging by the magnetic resonance device 10 may be continued without departing from the permitted operating range (e.g., without exceeding any potential limit values such as a maximum SAR value).

The current remaining time may be shown on the display unit 24, for example. Therefore, a physician, for example, who is carrying out an interventional procedure on the patient 15 may be notified about the current remaining time so that the same may instigate countermeasures in a timely manner prior to the critical event representing a danger to the patient. A position of an interventional instrument during the measurement for the purpose of medical imaging may be displayed by the display unit 24.

The acts 120 and 130 may be carried out repeatedly so that the current remaining time is the provisional actual residual time duration at every time point. The time intervals between the repetitions in acts 120 and 130 are consequently chosen so as to be sufficiently short.

FIG. 3 shows an expanded method. In act 140, a minimum remaining time is provided to the evaluation unit 27. The minimum remaining time may be input by the input unit 25 (e.g., by a physician and/or an operator). The minimum remaining time is advantageously dimensioned so as to be sufficient to implement a safe termination of a medical examination (e.g., an interventional procedure). It may be possible within the minimum remaining time, for example, to remove any potential interventional instruments from the body of the patient 15 under MR guidance.

In act 150, the current remaining time is compared with the minimum remaining time. Depending on an outcome of this comparison, an output signal is output in act 160. If it emerges from this comparison, for example, that the current remaining time is less than the minimum remaining time, a warning may be output, for example, with the output unit 24. The output unit 24 may also include an acoustic output capability for this purpose such as, for example, a loudspeaker.

The determination of the current remaining time may include an averaging. For example, a plurality of values determined by measurement (e.g., the measured values themselves and/or values derived from same) may be averaged. For example, all values over a predetermined time period, of one minute, for example, may be averaged, and the averaged value may be used for the further calculation of the current remaining time.

In one embodiment, the determination of a current remaining time may include a worst-case view. For example, the current remaining time may be estimated based on various types of input values (e.g., extrapolation information and/or models, and/or methods). To increase the safety of the patient 15, the least favorable remaining time resulting from same (e.g., generally the smallest) may be selected as the current remaining time.

Optionally, in act 170, depending on an outcome of the comparison of the current remaining time with the minimum remaining time in act 150, at least one measurement parameter of the pulse sequence of the instantaneous measurement for the purpose of medical imaging (e.g., the magnetic resonance measurement) such as, for example, a repetition time (TR) and/or a flip angle and/or a transmit voltage and/or a transmit mode may be changed. The changed pulse sequence makes it possible for the critical event to be favorably influenced, for example, by reducing the SAR.

In a further optional act 180, at least one changed measurement parameter may be restored in the case of the current remaining time being less than a minimum remaining time extended by a safety margin. The safety margin may be stored in the database 27 and/or input by the input unit 25.

As a result of the adaptation of the pulse sequence in act 170, preceding act 180, and/or as a result of changes independent of same such as, for example, a changing of the pulse sequence already envisioned independently of act 170, the current remaining time should increase (again). As soon as the current remaining time lies above a certain threshold (again), which is determined by the safety margin among other factors, the changes implemented in act 170 may be reversed again in act 180. This may be advantageous since the changes implemented in act 170 may possibly result in a worsening of the quality of the MR images.

FIG. 4 shows a further representation of a possible method for monitoring a magnetic resonance measurement 200 with possibly different partial sequences 210. The partial sequences may be described based on various measurement protocols.

In act 140, the physician and/or an operator configures the minimum remaining time (e.g., a minimum time that may be available for an MR-guided emergency evacuation and/or re-establishment of a safe patient condition in which MR imaging is no longer necessary).

In act 130, the critical event (e.g., the SAR) is monitored and/or extrapolated. To do this, a SAR estimation prior to starting the pulse sequence may be used and/or a SAR development may be extrapolated (e.g., by an averaging of online SAR values over a plurality of duty cycles of the running pulse sequence). As a result, the availability of the minimum remaining time may be ensured during the magnetic resonance measurement 200. This may be achieved, for example, based on sequence information (e.g., a preview over a succession of all envisioned sequence protocols) and/or by an extrapolation of the instantaneous online SAR values. A worst-case appraisal may be chosen to evaluate the current remaining time. An averaging of various SAR appraisals and/or previews may also be used. Advantageously, the user may configure how conservative the determination of the current remaining time should be.

In act 150, a check is carried out as to whether the threshold specified by the minimum remaining time is being exceeded. If so, then a visual and/or acoustic warning message is output in act 160 by which the physician and/or an operator is notified about the residual time in which further imaging is available.

In act 170, the physician and/or an operator may choose between various strategies to increase the available imaging time (e.g., at the expense of the quality and/or the speed of the imaging). For example, the flip angle and/or, in global terms, the transmit voltage of the high-frequency antenna unit 20 may be reduced. A further option includes an increase in the repetition time (TR). Where appropriate, the pTX transmit mode may be changed in as far as the magnetic resonance device 10 has a large number of HF transmit channels available. The original settings may be restored later if the minimum remaining time plus a safety margin is restored.

The method described in detail in the preceding and also the evaluation unit and magnetic resonance device constitute exemplary embodiments that may be modified in the most varied way by the person skilled in the art without departing from the scope of the invention. The use of the indefinite article "a" or "an," respectively, does not exclude the eventuality that the relevant features may also be present in multiple instances. The term "unit" does not exclude the eventuality that the relevant components consist of a plurality of interoperating sub components that may also be distributed spatially where appropriate.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining a current remaining time during a measurement for the purpose of medical imaging, the method comprising:
   providing a permitted operating range;
   providing an item of extrapolation information regarding at least one critical event, wherein the extrapolation information comprises an item of pulse sequence information and at least one value determined by measurement;
   determining, by an evaluation unit, the current remaining time based on the permitted operating range and the item of extrapolation information, such that the current remaining time is a time duration for continuing the measurement for the purpose of medical imaging within the permitted operating range, wherein a dependency between the item of pulse sequence information and the critical event is calibrated with the aid of the at least one value determined by measurement;
   providing a minimum remaining time, the minimum remaining time being a time period to allow for influencing the measurement for the purpose of medical imaging such that harm to a patient is avoided;

comparing, by the evaluation unit, the current remaining time with the minimum remaining time; and outputting an output signal as a function of an outcome of the comparison of the current remaining time with the minimum remaining time.

2. The method of claim 1, wherein the measurement for the purpose of medical imaging comprises a magnetic resonance measurement, a computed tomography measurement, an X-ray measurement, a mammography measurement, a positron emission tomography measurement, a single photon emission computer tomography measurement, a scintigraphy measurement, a sonography measurement, a thermography measurement, an electrical impedance tomography measurement, or any combination thereof.

3. The method of claim 1, wherein the at least one critical event comprises a heating of at least one body part of a patient caused by an energy absorption, a peripheral nerve stimulation of the patient, or the heating of the at least one body part of the patient caused by the energy absorption and the peripheral nerve stimulation of the patient.

4. The method of claim 1, further comprising displaying a position of an interventional instrument during the measurement for the purpose of medical imaging.

5. The method of claim 1, wherein the determination of the current remaining time comprises an averaging.

6. The method of claim 1, wherein the determination of the current remaining time comprises a worst-case view.

7. The method of claim 1, further comprising outputting a warning message as the output signal in the case of the current remaining time being less than the minimum remaining time.

8. The method of claim 1, further comprising changing a pulse sequence depending on the outcome of the comparison of the current remaining time with the minimum remaining time.

9. The method of claim 8, further comprising changing a repetition time, a flip angle, a transmit voltage, a transmit mode or a combination thereof of the pulse sequence.

10. The method of claim 8, further comprising restoring at least one changed measurement parameter in the case of the current remaining time being less than the minimum remaining time extended by a safety margin.

11. An evaluation unit comprising:
an arithmetic-logic unit configured to determine a current remaining time during a measurement for the purpose of medical imaging, the determination of the current remaining time comprising:
provision of a permitted operating range;
provision of an item of extrapolation information regarding at least one critical event, wherein the extrapolation information comprises an item of pulse sequence information and at least one value determined by measurement;
determination of the current remaining time based on the permitted operating range and the item of extrapolation information, such that the current remaining time is a time duration for continuing the measurement for the purpose of medical imaging within the permitted operating range, wherein a dependency between the item of pulse sequence information and the critical event is calibrated with the aid of the at least one value determined by measurement;
provision of a minimum remaining time, the minimum remaining time being a time period to allow for influencing the measurement for the purpose of medical imaging such that harm to a patient is avoided;
comparison, by the evaluation unit, of the current remaining time with the minimum remaining time; and
output of an output signal as a function of an outcome of the comparison of the current remaining time with the minimum remaining time.

12. A medical imaging device comprising:
an evaluation unit comprising:
an arithmetic-logic unit configured to determine a current remaining time during a measurement for the purpose of medical imaging, the determination of the current remaining time comprising:
provision of a permitted operating range;
provision of an item of extrapolation information regarding at least one critical event, wherein the extrapolation information comprises an item of pulse sequence information and at least one value determined by measurement;
determination of the current remaining time based on the permitted operating range and the item of extrapolation information, such that the current remaining time is a time duration for continuing the measurement for the purpose of medical imaging within the permitted operating range, wherein a dependency between the item of pulse sequence information and the critical event is calibrated with the aid of the at least one value determined by measurement;
provision of a minimum remaining time, the minimum remaining time being a time period to allow for influencing the measurement for the purpose of medical imaging such that harm to a patient is avoided;
comparison, by the evaluation unit, of the current remaining time with the minimum remaining time; and
output of an output signal as a function of an outcome of the comparison of the current remaining time with the minimum remaining time.

13. The medical imaging device of claim 12, further comprising a magnetic resonance device, a computed tomography device, an X-ray device, a mammography device, a positron emission tomography device, a single photon emission computer tomography device, a scintigraphy device, a sonography device, a thermography device, an electrical impedance tomography device, or any combination thereof.

14. A computer program product comprising a non-transitory computer-readable storage medium storing instructions executable by a programmable arithmetic-logic unit of an evaluation unit to determine a current remaining time during a measurement for the purpose of medical imaging, the instructions comprising:
providing a permitted operating range;
providing an item of extrapolation information regarding at least one critical event, wherein the extrapolation information comprises an item of pulse sequence information and at least one value determined by measurement;
determining the current remaining time based on the permitted operating range and the item of extrapolation information, such that the current remaining time is a time duration for continuing the measurement for the purpose of medical imaging within the permitted operating range, wherein a dependency between the item of pulse sequence information and the critical event is calibrated with the aid of the at least one value determined by measurement;

providing a minimum remaining time, the minimum remaining time being a time period to allow for influencing the measurement for the purpose of medical imaging such that harm to a patient is avoided;

comparing, by the evaluation unit, the current remaining time with the minimum remaining time; and outputting an output signal as a function of an outcome of the comparison of the current remaining time with the minimum remaining time.

* * * * *